United States Patent [19]

Schectman

[11] Patent Number: 5,326,369
[45] Date of Patent: Jul. 5, 1994

[54] FLEXIBLE ACTUATING SCREW

[76] Inventor: Leonard A. Schectman, 3742 Boanza Cir., Lantana, Fla. 33462

[21] Appl. No.: 898,089

[22] Filed: Jun. 12, 1992

[51] Int. Cl.⁵ .......................... A61F 2/54; A61F 2/70
[52] U.S. Cl. ...................... 623/24; 623/64; 74/89.15; 74/479 BP
[58] Field of Search .................. 623/64, 57, 24; 411/385, 394, 437; 74/89.15, 479 B, 479 BE, 479 BP, 479 BF, 479 BJ

[56] References Cited

U.S. PATENT DOCUMENTS

| | | | |
|---|---|---|---|
| 2,893,016 | 7/1959 | Zion | 623/57 X |
| 3,166,632 | 1/1965 | Woodman | 411/437 X |
| 3,877,341 | 4/1975 | Grimm | 411/437 |
| 4,364,593 | 12/1982 | Maeda | 623/64 X |

FOREIGN PATENT DOCUMENTS

| | | | |
|---|---|---|---|
| 0614241 | 2/1961 | Canada | 411/437 |
| 0807071 | 6/1951 | Fed. Rep. of Germany | 411/437 |

Primary Examiner—Randall L. Green
Assistant Examiner—D. Willse
Attorney, Agent, or Firm—Malin, Haley DiMaggio & Crosby

[57] ABSTRACT

A motor actuated screw device for the transmission of torque over articulating surfaces finding particular use in prosthetic devices used as mechanical artificial hands. The device employs a high torque motor mounted on a support platform which is attached to a cable or universal joint having at least one externally threaded cincture affixed to the cable. The placement of at least one articulating member hingedly mounted to the support platform with an internally threaded guide bushing affixed to the articulating member allows the cincture to be placed therethrough allowing the motion to rotate the cable/cincture causing the articulating member to rotate about the hinge connection to the support base. The use of multiple members attached to the articulating member together with hinges placed therebetween, allows the use of the instant device to move all of the members according to predetermined threaded engagement providing each member with nearly a direct torque transfer from the motor.

13 Claims, 5 Drawing Sheets

FLEXIBLE ACTUATING SCREW

FIELD OF THE INVENTION

This invention relates generally to motion transfer and, more particularly, to a flexible actuating screw providing high speed torque transfer having particular use in both small and large scale robotics.

BACKGROUND INFORMATION

Motion transfer by use of cable provides superior characteristics in pulling and rotation, but obviously flounders in its ability to push unless the cable is rigid or contained. Shielded cables provide a mechanism for pulling and pushing a flexible cable by use of a stationary casing element. However, the shielded cable must be supported at both ends and becomes inefficient if the cable includes any type of bend. These problems are exemplified when a cable is employed in either an intricate setting or large scale operation. For instance, a robotic hand is an intricate device made operational by motion transfer cabling. The shielded cable is impractical for the size of the device and need for extreme bends. Conversely, the unshielded cable must have a level of rigidity, making it limited in its ability to provide motion transfer in both directions.

U.S. Pat. No. 5,080,682, issued to the instant inventor, teaches the use of an artificial robotic hand employing cables for motion transfer, the disclosure is incorporated by reference herein as if fully restated hereinafter. One objective of the '682 Patent is to provide an artificial hand prosthesis having hinged or articulating fingers and a thumb. The device is dependant upon control cables for individual movement of each member. An electric motor is coupled to a linear gear rack which in turn is connected to a stiff cable drawn to the end of the finger. In operation, the motor moves the rack in a forward direction causing the finger to bend along the linkage joints, reversal of the motor causes the finger to straighten. The use of a shielded cable is not cost effective and the severe bending required by the fingers is impractical due to the friction caused by the shield.

Thus, what is needed is a means for transferring torque having articulating members with minimal loss in torque transfer having particular use in robotics and providing a means for large torque transfer using a frictionless lead screw arrangement.

SUMMARY OF THE INVENTION

The present invention satisfies this need through provision of a flexible lead screw device that provides motion transfer around corners without loss of propagated torque. In general the instant invention is a motor actuated screw capable of torque transmission over articulating surfaces. A high torque motor is mounted to a support platform which is attached to a cable having at least one externally threaded cincture affixed to the cable. The placement of at least one articulating member hingedly mounted to the support platform with an internally threaded guide bushing affixed to the articulating member allows the cincture to be placed therethrough allowing the motor to move the cincture causing the articulating member to rotate about the hinge in relation to its position to the support base. The use of multiple members attached to the articulating member allows the instant device to move all of the members according to predetermined threaded engagement providing each member with a near direct torque transfer from the motor.

Application of multiple members hingedly joined end to end provides the instant invention with a unique capability in positioning each of the members according to the rotational output of a motor. For instance, a typical application can be found in its use as an artificial hand prosthesis that includes a lightweight hand support platform sized to emulate the metacarpus of a human hand. Formation of a finger is performed by three lightweight aluminum bars hinged together and sized in length to approximate the phalanges for each of the fingers of the human hand in a similar manner as set forth in my U.S. Pat. No. 5,080,682. Each bar phalange includes a threaded guide bushing affixed or made a part of the phalange allowing the cincture of the cable to move the bar in accordance with the rotation of the motor. This allows the closing of the finger in the normal manner and reversal of the motor to straighten the finger to a predetermined position. If the threaded bushings are offset from the bar, the finger can be curled into either direction. Similarly, the finger can now be made to curl in a sideways manner as the connecting cable can be turned at any direction without affecting cable sensitively or operational functionality.

Accordingly, a primary object of the present invention is to provide a means for transferring torque about articulating members.

Still another object of the present invention is to provide a means for transferring torque about articulating members with minimal loss in torque transfer having particular use in prosthetic devices used as a mechanical artificial hand.

Yet still another object of the present invention is to provide a frictionless bushing for transferring torque over articulating members on large scale installations.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION

Although the invention has been described in terms a specific embodiment, it will be readily apparent to those skilled in this art that various modifications, rearrangements and substitutions can be made without departing from the spirit of the invention. The scope of the invention is defined by the claims appended hereto.

Figure 1:
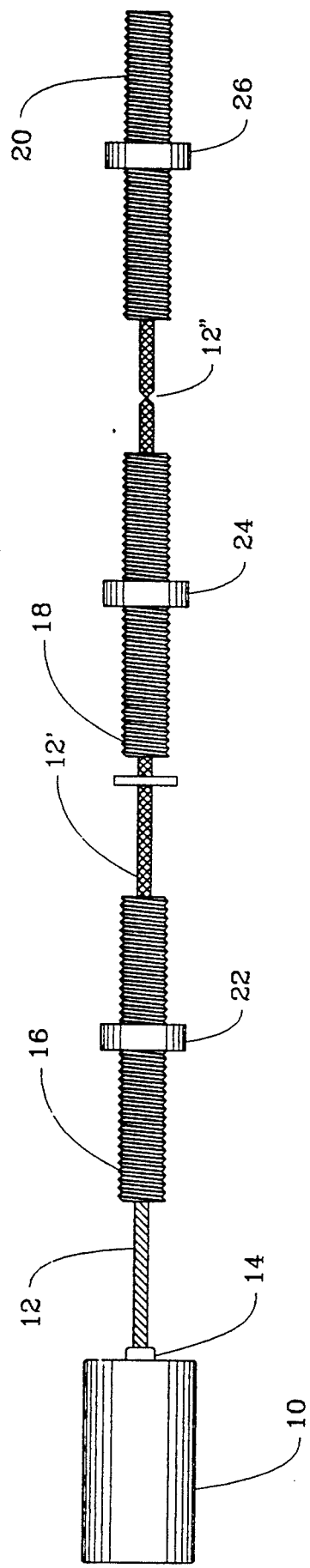
FIG. 1 is a diagrammatic representation of flexible lead screw system according to the instant invention in a center position.
Figure 2:
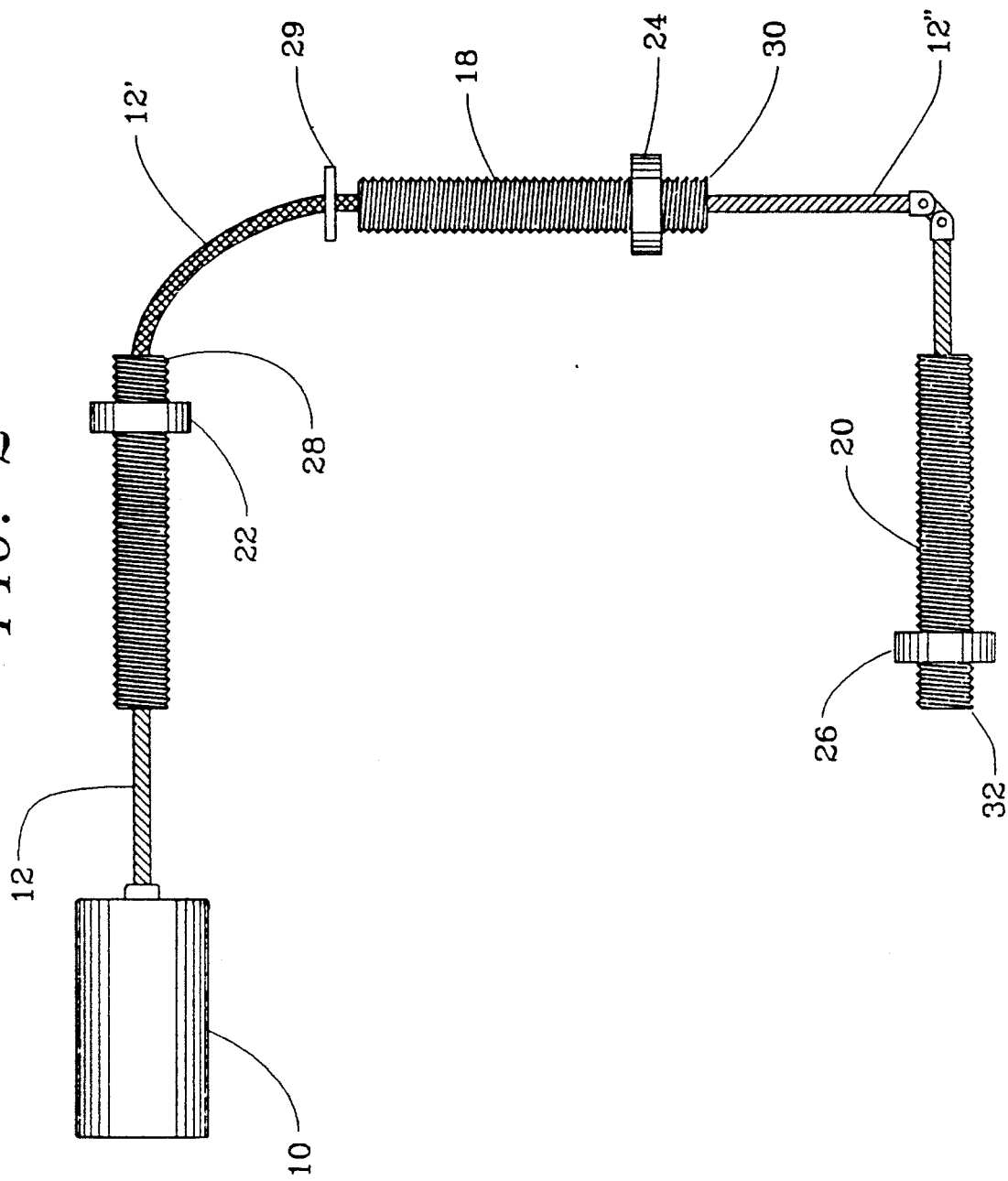
FIG. 2 is a diagrammatic representation of flexible lead screw system shown in FIG. 1 in an extended position.

Referring now to the drawings and specifically to FIGS. 1 and 2, shown is the motor actuated screw device of the instant invention wherein a high torque motor 10 with a cable or preferably a straight shaft 12 coupled directly to the rotational shaft 14 of motor 10. The shaft 12 is modified to include at least one externally threaded cincture 16 which is formed from a part of the shaft or permanently affixed thereto. For optimum use of this invention a plurality of cinctures are coupled to the shaft 12 by use of flexible cabling or universal joints allowing transmission around angular bends. Illustrated is cincture 18 which will provide the motion translation at a perpendicular position to cincture 16 while cincture 20 provides motion translation at a perpendicular position to cincture 18. To create motion of an articulating member, internally threaded guide bushing 22 is affixed to a first articulating member that is hingedly attached to a motor base, shown by example later in this description, which is operatively associated with cincture 16. Clockwise rotation of the shaft 12 causes cincture 16 to rotate, the threaded interface forcing threaded guide bushing 22 away from the motor, which due to the hinge coupling, results in the articulation of the member attached to the guide bushing 22. Similarly, the threaded interface forces threaded guide bushing 24, which when coupled to the member attached to guide bushing 22, results in the articulation of the member attached to the guide bushing 24. Further, the threaded interface forces threaded guide bushing 26, which when coupled to the member attached to guide bushing 24, results in the articulation of the member attached to the guide bushing 26.

FIG. 2 illustrates the diagrammatic representation of flexible lead screw system fully rotated in which motor 10 with shaft 12 is rotated which in turn causes guide bushing 22 to move in relation to threaded cincture 16 shortening the dimensional distance between guide bushing 22 and end 28. Flexible cable 12' allowing an angular curve between cinctures 16 and 18. A centering sleeve 29 can be used to prefix each cincture for optimum centering. Rotation of cable 12' causes guide bushing 24 to move in relation to threaded cincture 18 shortening the dimensional distance between guide bushing 24 and end 30. Universal joint 12" allows an angular curve between cinctures 18 and 20. Rotation of the universal joint 12" causing guide bushing 26 to move in relation to threaded cincture 20 shortening the dimensional distance between guide bushing 26 and end 32. The universal joint may consist of two stiff shafts with a mechanical bearing attachment disposed therebetween or a stiff cables with an elastomer forming a flexible joint therebetween. Each cincture can be defined as a uniformly threaded rod permanently attached to the cable having external threads engageable with the cable guide bushings, or alternatively, each cincture may have a different thread pitch ration to vary the speed of movement of each guide bushing and respective attached member. Threads per inch can be varied upon industry standards, i.e. 8, 14, 18, 27 or employ custom thread per inch for various speeds. Fine pitch threads provide maximum sensitivity and torque transfer. Wide spaced pitch threads provide greater speed of movement. Control of the motor allows for positioning although a variable speed motor provides various speed ratios. It should be noted that cabling between cinctures as defined by 12, 12' and 12" may consist of flexible, stiff, universal joints, or any combination thereof for transmission of the torque around a bend. The type of motion transfer is dependant upon the load and the combination illustrated is for example purposes only.

Figure 3:
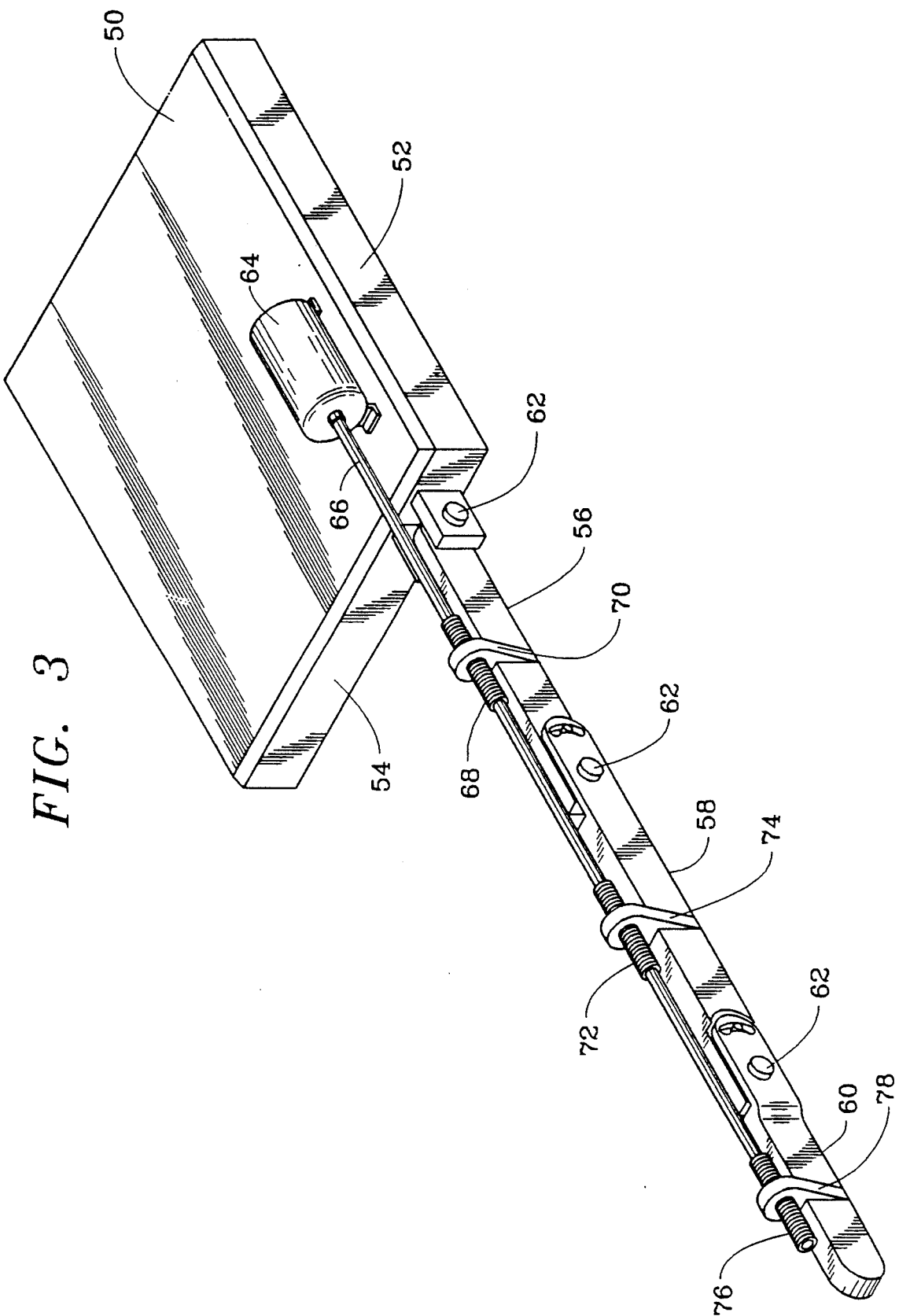
FIG. 3 is a perspective view of the invention used as an actuating mechanism for a robotic hand.

Now referring to FIG. 3, shown is an example of the motor actuated screw device of the instant invention used for the transmission of torque over articulating surfaces for simulating the movement of a human hand. Support platform 50 is sized to resemble a human metacarpus having a first end 52 and a first side 54 next to said first end 52. The actuation of the index finger includes phalange aluminum support bars 56, 58, and 60, connected by hinge pins 62 movably connected to simulate the movement of human finger to the first end 54 of the support platform 50. Shown is high torque motor 64 mounted on the support platform 50 with an individual cable 66 coupled to the motor 64 with a first cincture 68 affixed to the cable 66 and rotatably coupled to first hinge member 56 by means of fixed cable guide bushing 70. Second cincture 72 affixed to the cable 6 and rotatably coupled to second hinge member 58 by means of fixed cable guide bushing 74. Third cincture 76 affixed to the cable 66 and rotatably coupled to third hinge member 60 by means of fixed cable guide bushing 78.

Figure 4:
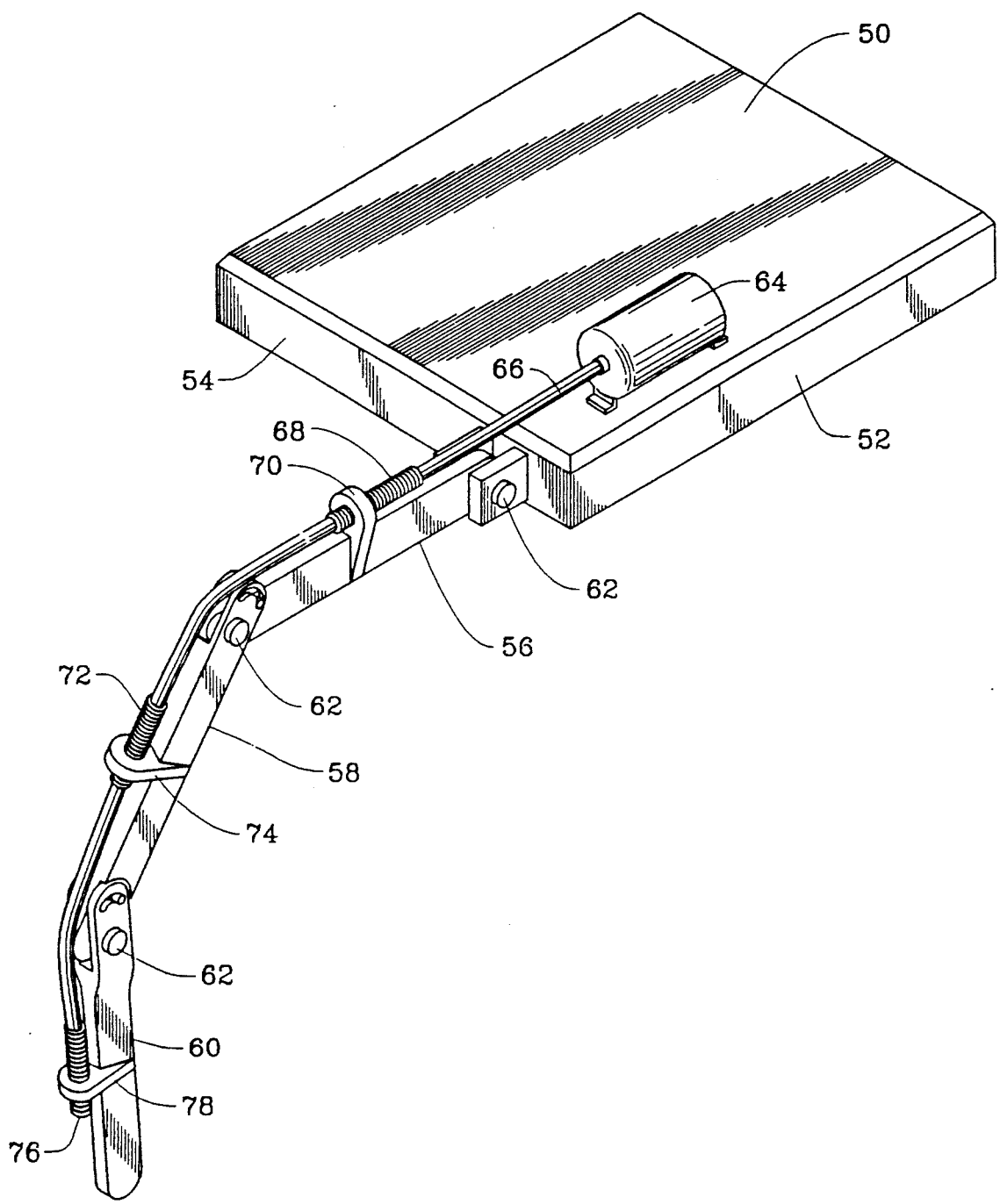
FIG. 4 is a perspective view of the invention shown in FIG. 3 with the actuating mechanism extended.

Operation of the motor actuated screw device as an electro-mechanical grasping device for simulating the movement of a human hand for an artificial hand prosthesis is shown in FIG. 4. The actuation of the index finger requires the motor 64 to rotate wherein cable 66 is coupled first cincture 68 and rotatably coupled to first hinge member 56 by means of fixed cable guide bushing 70. Second cincture 72 affixed to the cable 66 and rotatably coupled to second hinge member 58 by means of fixed cable guide bushing 74. Third cincture 76 affixed to the cable 66 and rotatably coupled to third hinge member 60 by means of fixed cable guide bushing 78. Rotation of cable 66 causes guide bushing 70 to move in relation to threaded cincture 68 forcing the first member 56 downward, similarly cincture 72 forces the second member 58 downward in relation to bushing 74 as well as causing third support member 60 inward in relation to bushing 78 by the rotation of cincture 78.

Figure 5:
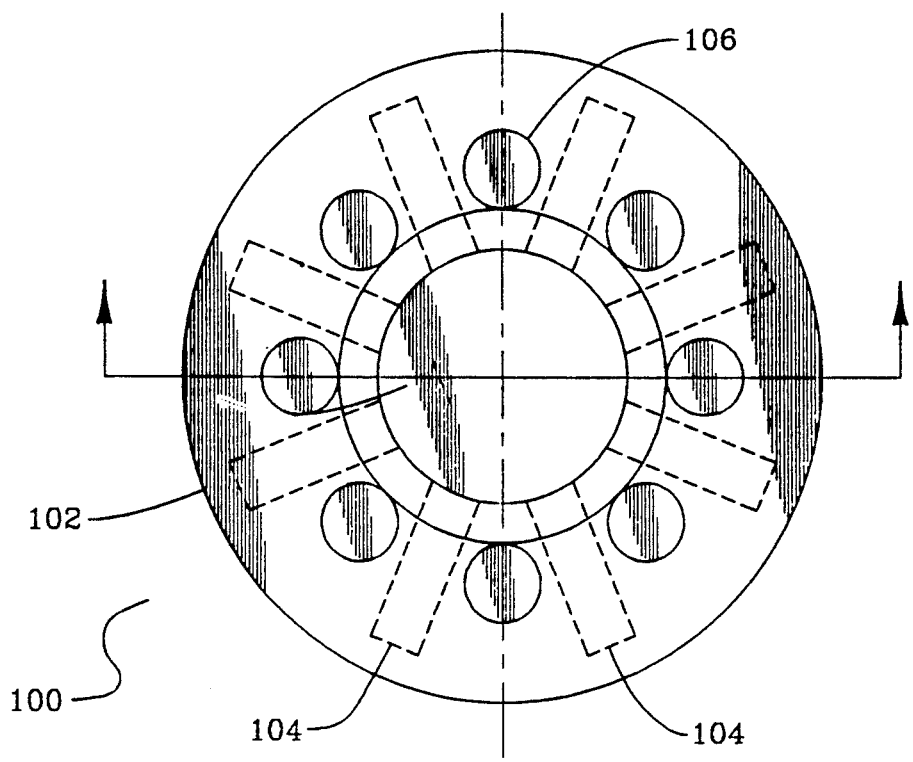
FIG. 5 is the top plan view of a bearing bushing for alternative use in the instant invention.
Figure 6:
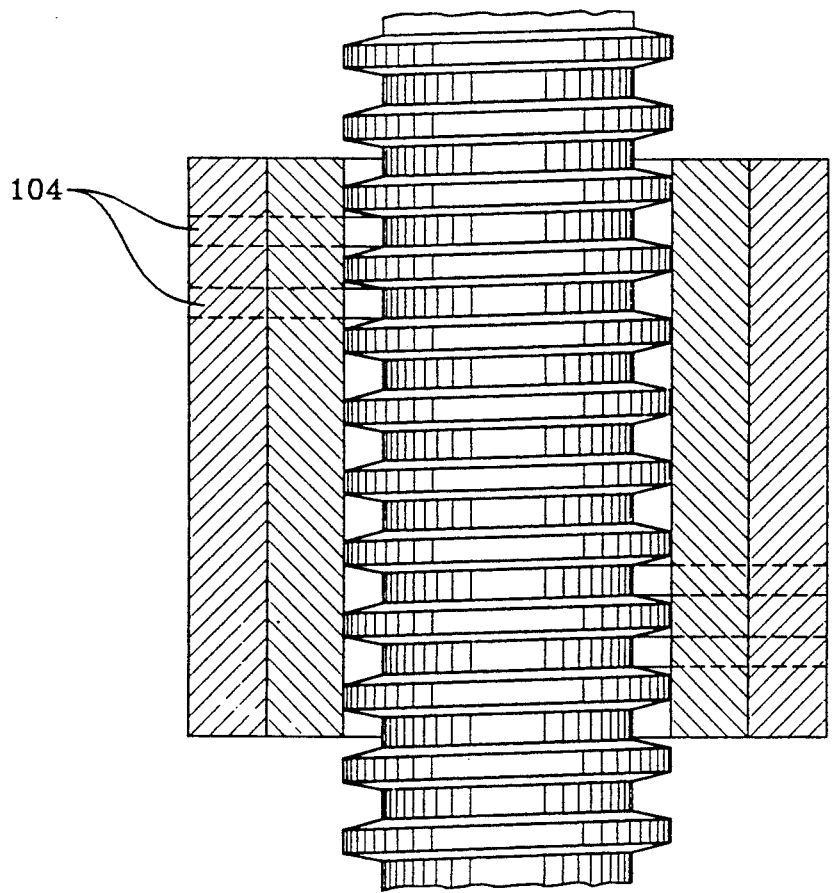
FIG. 6 is a cross sectional side view of the bearing bushing shown in FIG. 5.

FIG. 5 and 6 illustrate a bearing guide bushing can replace the threaded guide bushings described above for large scale operations. The bearing bushing 100 includes a support structure 102 with a plurality of horizontal bearings 104 staggered to lead the screw tread of the cincture. The actual number of bearings is dependant upon the required load or torque required during transfer. The greater the number of horizontal bearings dramatically increases the dynamic capacity of the guide bushing for push and pull purposes. The remainder of the bushing is comprised of vertical sleeve or roller bearings 106 set in an angular position allowing the threaded portion of the cincture to carry through the bearing support without friction. The vertical bearings reduce frictional contact with the side walls in all instances where horizontal bearings are not provided for motion transfer.

It is to be understood that while I have illustrated and described certain forms of my invention, it is not to be limited to the specific forms or arrangement of parts herein describe and shown. It will be apparent to those skilled in the art that various changes may be made without departing from the scope of the invention and the invention is not to be considered limited to which is shown in the drawings and described in the specification.

What I claim is:

1. A motor actuated screw device for the transmission of torque over articulating surfaces comprising:
   at least one high torque motor mounted on a support platform;
   a cable means directly coupled to said high torque motor, said cable having a plurality of externally threaded cinctures coupled to said cable;
   at least one articulating member hingedly mounted to said support platform;
   at least one internally threaded cable guide bushing fixedly attached to said articulating member and operatively associated with said cinctures; and
   a means for controlling the directional rotation of said motor, said motor causing the rotation of said cable and said threaded cinctures through said threaded guide bushing, causing said articulating member attached to said guide bushing to move in direct response to said motor rotation.

2. The motor actuated screw device according to claim 1 wherein each of said cinctures is further defined as a threaded rod permanently attached to said cable means having external threads engageable with said cable guide bushing.

3. The motor actuated screw device according to claim 1 wherein said cable means is defined as a stiff shaft.

4. The motor actuated screw device according to claim 1 wherein said cable means is defined as a flexible cable.

5. The motor actuated screw device according to claim 1 wherein said cable means is defined as a universal joint.

6. The motor actuated screw device according to claim 1, wherein the threads of said externally threaded cinctures and said internally threaded cable guide bushing are finely spaced pitched threads for maximum sensitivity and torque transfer.

7. The motor actuated screw device according to claim 1, wherein the threads of said externally threaded cinctures and said internally threaded cable guide bushing are widely spaced pitched threads for speed of articulation.

8. The motor actuated screw device according to claim 1, wherein the threads of said externally threaded cinctures and said internally threaded cable guide bushing are selected according to the desired rotation speed and load condition of an individual member of an articulating arm.

9. The motor actuated screw device according to claim 1, wherein said at least one articulating member is further defined as a plurality of support bars, each of said support bars having a first end and a second end, a first one of said support bars having its first end hingedly attached to said platform and its second end hingedly attached to the first end of a second one of said support bars.

10. The motor actuated screw device according to claim 9, wherein said support bars include at least one joining support bar having hinge pins on each of said first an second ends and an end support bar having a hinge pin coupled to one of said joining support bars.

11. The motor actuated screw device according to claim 1, wherein each of said at least one bushing is defined as a bearing support having a plurality of horizontal bearings disposed therein for engagement with the threads of a cincture and a plurality of vertical bearings set at the thread pitch to provide a frictionless bearing.

12. The motor actuated screw device according to claim 11 wherein said vertical bearings of said bearing support are roller bearings.

13. A motor actuated screw device for the transmission of torque over articulating surfaces for use in an electro-mechanical grasping device for simulating the movement of a human hand as an artificial hand prosthesis, said device comprising:
   a support platform sized to resemble a human metacarpus, said support platform having a first end and a first side next to said first end;
   a plurality of extended hinged members movably connected to simulate the movement of a human finger, a first one of said hinged members connected to said first end of said support platform, said extended hinged members including a first bar, a second bar, and a third bar, each of said first, second, and third bars being hingedly joined together from end to end;
   a plurality of high torque motors, each of said motors mounted on said support platform;
   individual cable means coupled to each of said high torque motors, each said cable having a plurality of threaded cinctures affixed thereto and rotatably coupled to each of said hinged members by means of fixed cable guide bushings, said guide bushings having internal threads for receiving and guiding said cable mounted cinctures;
   means for controlling said threaded cables connected to each of said motors;
   said extended hinged members being sized to correspond to the digits in a human hand, and located relative to said support platform to approximate the location of human fingers;
   said first, second, and third bars sized to correspond to the phalanges in the fingers of a human hand;
   whereby said hinged members can be individually moved to positions simulating human finger movement through the action of said threaded cables and cable bushings attached to said hinged members simulating movement of the human hand.

* * * * *